United States Patent [19]

Chance et al.

[11] Patent Number: 5,782,755
[45] Date of Patent: Jul. 21, 1998

[54] MONITORING ONE OR MORE SOLUTES IN A BIOLOGICAL SYSTEM USING OPTICAL TECHNIQUES

[75] Inventors: Britton Chance, Marathon, Fla.; Hanli Liu, Philadelphia, Pa.

[73] Assignee: Non-Invasive Technology, Inc., Philadelphia, Pa.

[21] Appl. No.: 349,839

[22] Filed: Dec. 2, 1994

Related U.S. Application Data

[63] Continuation-in-part of Ser. No. 150,084, Nov. 15, 1993.

[51] Int. Cl.$^6$ .................................... A61B 5/00
[52] U.S. Cl. .................. 600/322; 600/473; 600/476
[58] Field of Search ................. 128/633, 664, 128/665; 356/39, 40, 41

[56] References Cited

U.S. PATENT DOCUMENTS

| | | |
|---|---|---|
| 4,014,321 | 3/1977 | March . |
| 4,029,085 | 6/1977 | DeWitt et al. . |
| 4,223,680 | 9/1980 | Jöbsis . |
| 4,281,645 | 8/1981 | Jöbsis . |
| 4,321,930 | 3/1982 | Jöbsis et al. . |
| 4,576,173 | 3/1986 | Parker et al. . |
| 4,655,225 | 4/1987 | Dähne et al. . |
| 4,700,708 | 10/1987 | New, Jr. e al. . |
| 4,714,341 | 12/1987 | Hamaguri et al. . |
| 4,773,422 | 9/1988 | Isaacson et al. . |
| 4,800,495 | 1/1989 | Smith . |
| 4,800,885 | 1/1989 | Johnson . |
| 4,836,207 | 6/1989 | Bursell et al. . |
| 4,846,183 | 7/1989 | Martin . |
| 4,869,254 | 9/1989 | Stone et al. . |
| 4,880,304 | 11/1989 | Jaeb et al. . |
| 4,908,762 | 3/1990 | Suzuki et al. . |
| 4,926,867 | 5/1990 | Kanda et al. . |
| 4,972,331 | 11/1990 | Chance . |
| 5,057,695 | 10/1991 | Hirao et al. ............... 128/633 |
| 5,119,815 | 6/1992 | Chance . |
| 5,178,142 | 1/1993 | Harjunmaa et al. ............ 128/633 |
| 5,277,181 | 1/1994 | Mendelson et al. ............ 128/633 |
| 5,497,769 | 3/1996 | Gratton et al. ................ 128/633 |
| 5,551,422 | 9/1996 | Simonsen et al. .............. 128/633 |

FOREIGN PATENT DOCUMENTS

| | | |
|---|---|---|
| 0 102 816 | 3/1984 | European Pat. Off. . |
| 25 38 985 | 5/1976 | Germany . |
| WO 92/20273 | 11/1992 | WIPO . |

OTHER PUBLICATIONS

Haida et al., "A New Method to Estimate the Ratio of Absorption Coefficients of Two Wave Lengths Using Phase Modulating NIR Spectroscopy," abstract submitted to ISOTT in Mainz, Germany, 1992.

Haida et al., "A Method to Estimate the Ratio of Absorption Coefficients of Two Wavelengths Using Phase–Modulated Near Infrared Light Spectroscopy," *Analytical Biochemistry*, 208:348–351, 1993.

(List continued on next page.)

*Primary Examiner*—Jennifer Bahr
*Assistant Examiner*—Eric F. Winakur
*Attorney, Agent, or Firm*—Fish & Richardson P.C.

[57] ABSTRACT

A scheme for monitoring one or more solutes in a biological system comprising the steps of: delivering light into a biological system containing one or more solutes, the light having a wavelength selected to be in a range wherein at least one of the one or more solutes is substantially non-absorbing; detecting at least first and second portions of the delivered light, the first portion having traveled through the biological system along one or more paths characterized by a first average path length, and the second portion having traveled through the biological system along one or more paths characterized by a second average path length that is greater than the first average path length; and comparing the first and second portions of the delivered light to monitor a concentration of one or more of the solutes in the biological system. Also described are schemes for monitoring low molecular weight polyhydroxy solutes, generally sugars (mannitol, fructose, sucrose, glucose), alcohols (methanol and propanediol), and electrolytes (sodium and potassium chloride).

50 Claims, 13 Drawing Sheets

OTHER PUBLICATIONS

Haida et al., "A Method to Estimate the Ratio of Absorption Coefficients of Two Wavelengths Using Phase Modulated Near Infrared Light Spectroscopy," *Adv. Exp. Biol. and Med.*, 345:829–835, 1994.

Patterson et al., "Time resolved reflectance and transmittance for the non-invasive measurement of tissue optical properties," *Applied Optics*, 28(12):2331–2336.

Sevick et al., "Quantitation of Time– and Frequency–Resolved Optical Spectra for the Determination of Tissue Oxygenation," Analytical Biochemistry, 195:330–351, 1991.

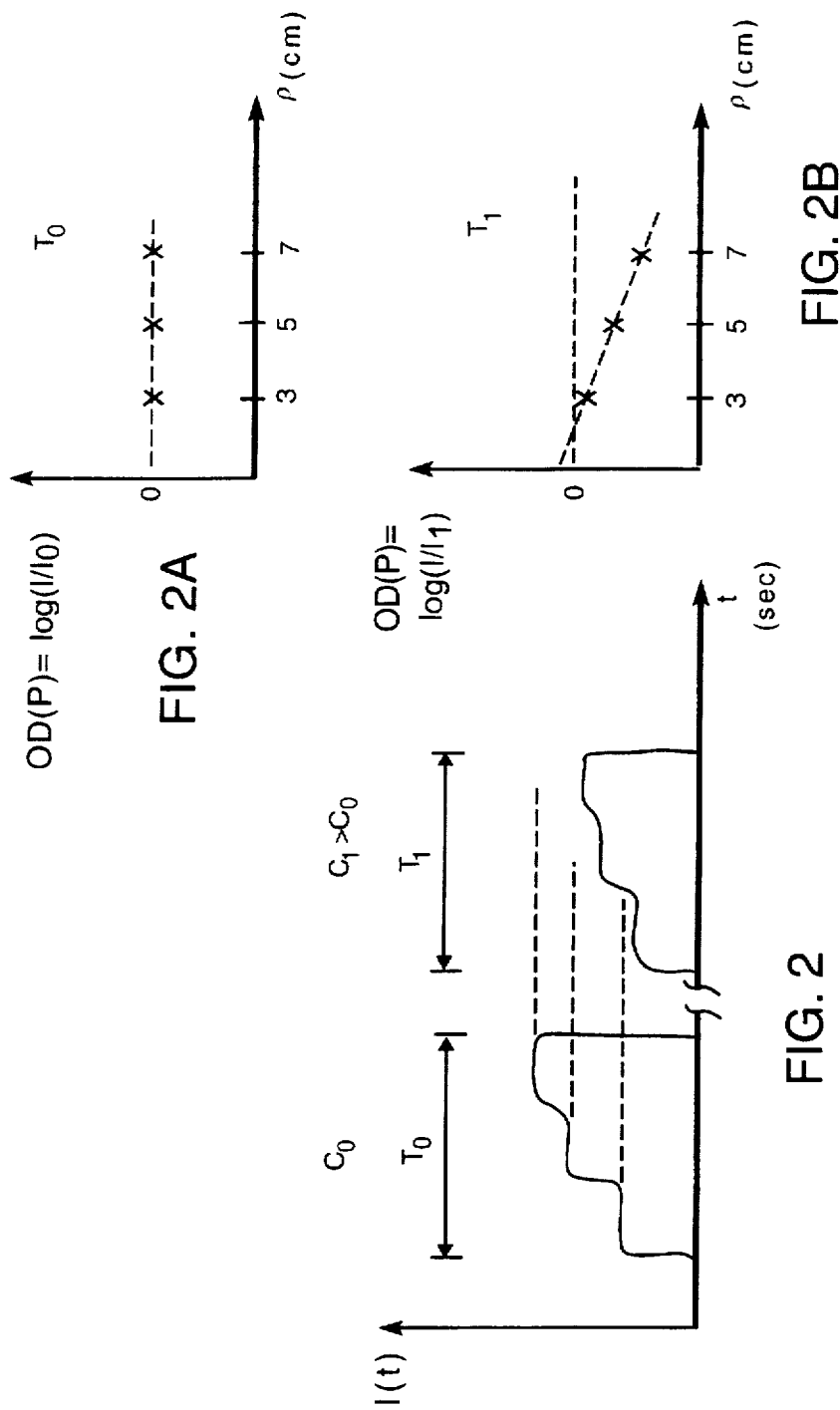

| concentration of intralipid(%) | 0.1 | 0.6 | 1 | 1.3 | 1.5 |
|---|---|---|---|---|---|
| slope/glucose(e-40D/mM/cm) | -0.27 | -1.02 | -1.56 | -1.88 | -2.05 |
| S.D | 0.0037 | 0.014 | 0.037 | 0.088 | 0.071 |
| slope/glucose/%IL(e40D/mM/cm/%IL) | -2.7 | -1.7 | 1.56 | -1.45 | -1.37 |
| intercept/glucose(e-40D/mM) | 0.98 | 0.29 | 0.91 | 1.94 | 3.7 |
| S.D | 0.15 | 0.083 | 0.09 | 0.36 | 0.27 |

FIG. 6

| | yeast=1.4% | | | yeast=2.8% | | 1%IL+1.4%yeast |
|---|---|---|---|---|---|---|
| scatterer | | | | | | |
| solute | mannitol | CH3OH* | NaCl | MOPS | water | KCl | mannitol |
| solute conc. range(M) | 0.2 | 4.5 | 3.9 | 0.21 | 27% | 1.74 | 0.4 |
| slope(e-40D/mM/cm) | -1.11 | -0.052 | -0.16 | -1.25 | -0.033 | -0.55 | -1.77 |
| S.D. | 0.085 | 0.0072 | 0.0065 | 0.11 | 0.0014 | 0.038 | 0.036 |
| Intercept(e-40D/mM) | 1.40 | 0.12 | 0.26 | 1.73 | 0.038 | 0.73 | 1.58 |
| S.D. | 0.17 | 0.048 | 0.0023 | 0.13 | 0.0013 | 0.036 | 0.13 |

* corrected for dilution

FIG. 10

| | IL=0.6% | | | IL=1% | |
|---|---|---|---|---|---|
| scatterer | | | | | |
| solute | mannitol | fructose | propanediol* | water | NaCl |
| solute conc. range(M) | 0.18 | 0.12 | 1.24 | 27% | 6.3 |
| slope(e-40D/mM/cm) | -1.03 | -1.27 | -0.25 | -0.038 | -0.29 |
| S.D. | 0.019 | 0.042 | 0.023 | 0.0013 | 0.021 |
| intercept(e-40D/mM) | 0.44 | 0.92 | 0.03 | 0.024 | 0.1 |
| S.D. | 0.063 | 0.12 | 0.004 | 0.0019 | 0.011 |

*corrected for dilution

FIG. 11

MONITORING ONE OR MORE SOLUTES IN A BIOLOGICAL SYSTEM USING OPTICAL TECHNIQUES

CROSS-REFERENCE TO RELATED APPLICATIONS

This application is a continuation-in-part of U.S. Ser. No. 08/150,084, filed Nov. 15, 1993, which is herein incorporated by reference.

BACKGROUND

This invention relates to in vivo monitoring one or more solutes in a biological system using optical techniques.

Monitoring the concentration of a solute (e.g., low molecular weight polyhydroxy solutes, generally sugars (mannitol, fructose, sucrose, glucose), alcohols (methanol and propanediol), and electrolytes (sodium and potassium chloride)) in a biological system has important applications in the medical field. For example, it is important for diabetics, who have gone off insulin, to monitor their glucose level so that can remedy any serious deviation in the level before harm occurs.

Near infra-red radiation (NIR) has been used to study non-invasively the oxygen metabolism in tissue (for example, the brain, finger, or ear lobe). Using visible, NIR and infra-red (IR) radiation for medical imaging could bring several advantages. In the NIR or IR range the contrast factor between a tumor and a tissue is much larger than in the X-ray range. In addition, the visible to IR radiation is preferred over the X-ray radiation since it is non-ionizing; thus, it potentially causes fewer side effects. However, with lower energy radiation, such as visible or infra-red radiation, the radiation is strongly scattered and absorbed in biological tissue, and the migration path cannot be approximated by a straight line, making inapplicable certain aspects of cross-sectional imaging techniques.

Near infrared spectroscopy has been used for monitoring the oxygen saturation of living tissue non-invasively. Since biological tissue has a high effective scattering factor ($\mu_s'$), the light travels a relatively long path making it difficult to compute the absorption coefficient ($\mu_a$) by usual methods.

SUMMARY

In a general aspect, the invention features a scheme for monitoring one or more solutes in a biological system comprising the steps of: delivering light into a biological system containing one or more solutes, the light having a wavelength selected to be in a range wherein at least one of the one or more solutes is substantially non-absorbing; detecting at least first and second portions of the delivered light, the first portion having traveled through the biological system along one or more paths characterized by a first average path length, and the second portion having traveled through the biological system along one or more paths characterized by a second average path length that is greater than the first average path length; and comparing the first and second portions of the delivered light to monitor a concentration of one or more of the solutes in the biological system.

Embodiments of the invention may include one or more of the following features. Comparing the first and second portions of the delivered light preferably comprises obtaining a characterization of the biological system based on a linear model relating an optical characteristic of the biological system and the first and second average path lengths. The characterization that is obtained may be the slope and/or the intercept of a line determined by fitting to the linear model measured characteristics of the first and second portions of light and distances representative of the first and second path lengths. Obtaining a characterization may comprise obtaining measures of first and second optical densities of the biological system based on the first and second portions of detected light and fitting the measures of optical densities to the generally linear model. Comparing the first and second portions of the delivered light may comprise determining a measure of the concentration of one or more of the solutes based on a comparison of the characterization of the biological system against a predetermined scale.

The monitoring scheme may further comprise determining a measure of a concentration of one or more of the solutes in the biological system based on a predetermined concentration scale. Detecting the first and second portions of the delivered light preferably comprises measuring first and second intensities ($I_1$, $I_2$) corresponding to the intensities of the first and second portions of light, respectively.

The monitoring scheme may further comprise determining changes, over time, in the first and second intensities ($I_1$, $I_2$) relative to first and second reference intensities ($I_{1,ref}$, $I_{2,ref}$). Determining relative changes in the first and second intensities may further comprise respectively determining first and second optical densities ($OD_1$, $OD_2$):

$$OD_1 = \log\left(\frac{I_1}{I_{1,ref}}\right)$$

$$OD_2 = \log\left(\frac{I_2}{I_{2,ref}}\right).$$

Comparing the first and second portions of the delivered light may comprise using a linear model relating the first and second optical densities to distances ($\rho_1$, $\rho_2$) representative of the first and second average path lengths to obtain a characterization of the biological system representative of the concentration of one or more of the solutes in the biological system. The characterization that is obtained is a slope (m) may be determined by $$m = \frac{OD_2 - OD_1}{\rho_2 - \rho_1}.$$

The characterization that is obtained may be an intercept (b) determined by $$b = \frac{OD_1 \cdot \rho_2 - OD_2 \cdot \rho_2}{\rho_2 - \rho_1}.$$

The monitoring scheme may further comprise detecting a third portion of the delivered light, the third portion having traveled through the biological system along one or more paths characterized by a third average path length that is greater than the first and second average path lengths.

In another aspect, the invention features a system for monitoring one or more solutes in a biological system comprising: at least two sources of light having a wavelength selected to be in a range wherein at least one of the one or more solutes is substantially non-absorbing, a detector positioned at different distances with respect to the at least two detectors to detect at least first and second portions of the delivered light, the first portion having traveled through the biological system along one or more paths characterized by a first average path length, and the second portion having traveled through the biological system along one or more paths characterized by a second average path length that is greater than the first average path length, and a comparator adapted to compare the first and second portions of the delivered light to monitor a concentration of one or more of the solutes in the biological system.

In one embodiment of the invention, two or more continuous light sources are used and light reflectance at separated input-output distances are measured. Approximation of the exact solution for the spatially resolved reflectance at separations larger than 2.5 cm provides a linear relationship between the separation and absorbance variation with respect to a reference sample. Slope and intercept of this straight line are functions of the absorption and scattering coefficients ($\mu_a$ and $\mu_s'$) of the measured sample. Using this technique, high measurement sensitivities for solute concentrations in a biological system can be achieved. For example, absorbency changes of approximately 0.2 milli OD are obtained for a 1 millimolar concentration change of the solute and per 1% change of the intralipid concentration.

Solutes contained in a biological system respond to migrating near-infrared and infrared light by acting primarily to scatter the applied light. The signal intensity of such migrating light is affected to a greater extent the longer the average path length migrated by the detected light. This enables us to obtain a linear relationship between an optical parameter of the biological system and at least two distances representative of average path lengths traveled by the detected light through the biological system (e.g., at least two different source detector spacing).

Other features and advantages will become apparent from the following description and from the claims.

DESCRIPTION

FIG. 2 is a plot of intensity as a function of time at two different time periods ($T_0$, $T_1$) during which the solute concentration level increased from $C_0$ to $C_1$.

FIGS. 2A and 2B are plots of optical density (OD) as a function of detector-light source separation ($\rho$) corresponding to the time periods ($T_0$, $T_1$) of FIG. 2.

FIG. 6 is a table indicating the optical effect of intralipid concentration upon glucose in the concentration range of 160 mM.

FIG. 10 is a table of baker's yeast as a scatterer and various solutes.

FIG. 11 is a table indicating the optical effect of a variety of solutes.

Figure 1A:
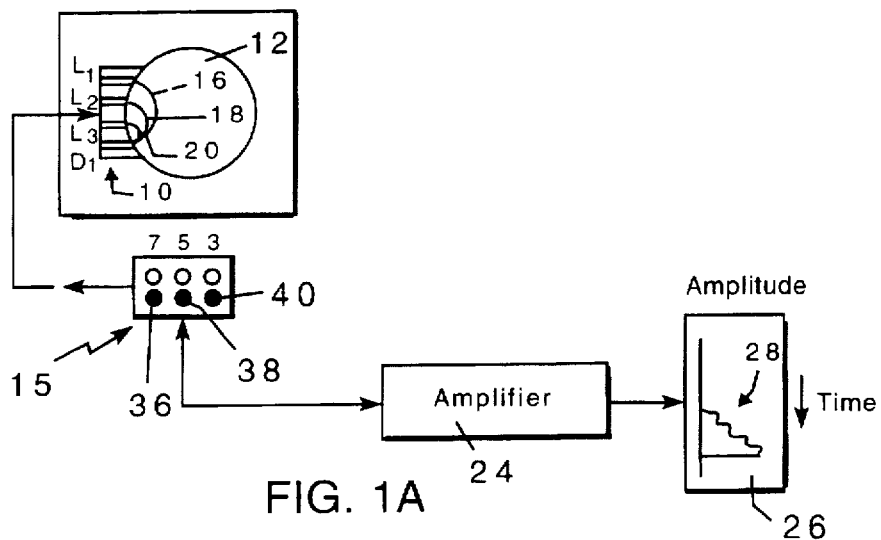
FIG. 1A is a diagrammatic sectional view of the monitor of FIG. 1 taken along the line 1A—1A.
Figure 1B:
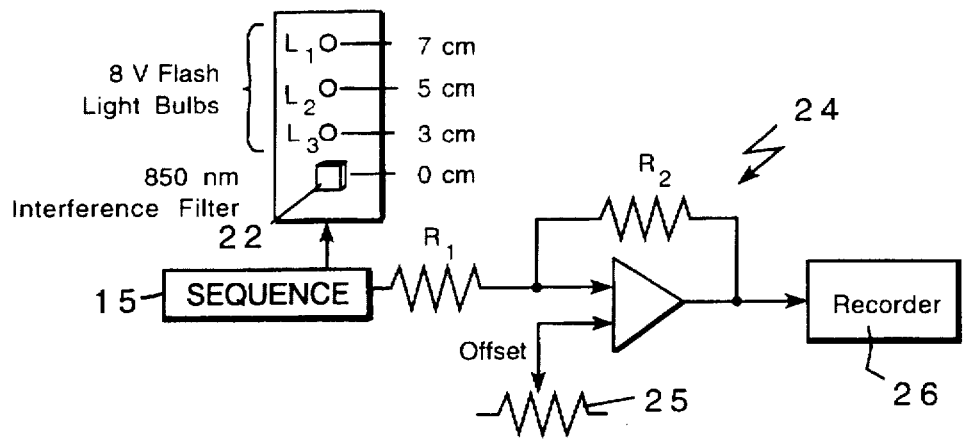
FIG. 1B is a diagrammatic side view of the monitor shown in FIG. 1A.
Figure 1:
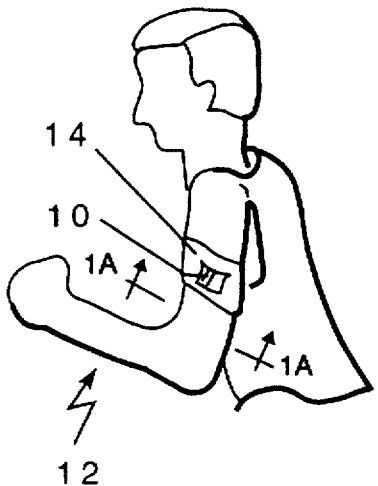
FIG. 1 is a diagrammatic side view of a monitor attached to the arm of a patient for monitoring the concentration of one or more solutes in the patient.

Referring to FIG. 1, a monitor 10 is attached to the surface of a biological system 12 (e.g., the arm of a patient) for non-invasively monitoring the concentration of one or more solutes (e.g., glucose) in the patient by using a novel optical technique. Monitor 10 is attached to the patient's arm by an adhesive bandage 14, although other means of attachment may be used (e.g., a stretchable arm wrap). Monitor 10 may be attached to other regions of the patient's body, e.g., head, breast, finger or belly, depending on the solute to be monitored and, e.g., the comfort level of the patient. Preferably the location of the monitor is selected to be where the extravascular solute level equilibrates with nearby blood vessels at a relatively rapid rate.

Monitor 10 uses a continuous light method and comprises a single detector DC amplifier system. This monitoring scheme has produced results that are compatible in sensitivity to those achievable by frequency-domain and time-domain methods. The signal-to-noise level of the changes observed with continuous light is ~0.01 milli OD at 850 nm with a 0.2 Hz bandwidth.

Referring to FIG. 1A, in a presently preferred embodiment, monitor 10 includes three spaced-apart light sources ($L_1$, $L_2$ and $L_3$; e.g., 8 volt flashbulbs) and a detector ($D_1$; e.g., a silicon photodiode). The light sources are respectively spaced different distances ($\rho_1$, $\rho_2$ and $\rho_3$, respectively) from the detector. For example, in the embodiment shown, $\rho_1$, $\rho_2$ and $\rho_3$ are equal to 7 cm, 5 cm and 3 cm, respectively.

The light sources deliver light into the patient's arm in sequence, which is controlled by a sequencer 15, and the delivered light migrates though a region of the patient's arm to the detector along one or more paths that can be respectively characterized by average path lengths 16, 18, 20. The distances between the light sources and the detector ($\rho_1$, $\rho_2$ and $\rho_3$) are respectively representative of these average path lengths. The lamp spacings from the detector may be varied, depending, e.g., on the size of the monitored region and on intrinsic noise levels. In certain preferred embodiments, the lamps should be spaced far enough apart to take advantage of the spacing effect and thus enhance the measurement accuracy. Although, in certain applications it is preferred that the lamps be spaced from the detector by at least 2 cm to achieve a simplification in the mathematics used to derive the solute concentration.

Figure 1C:
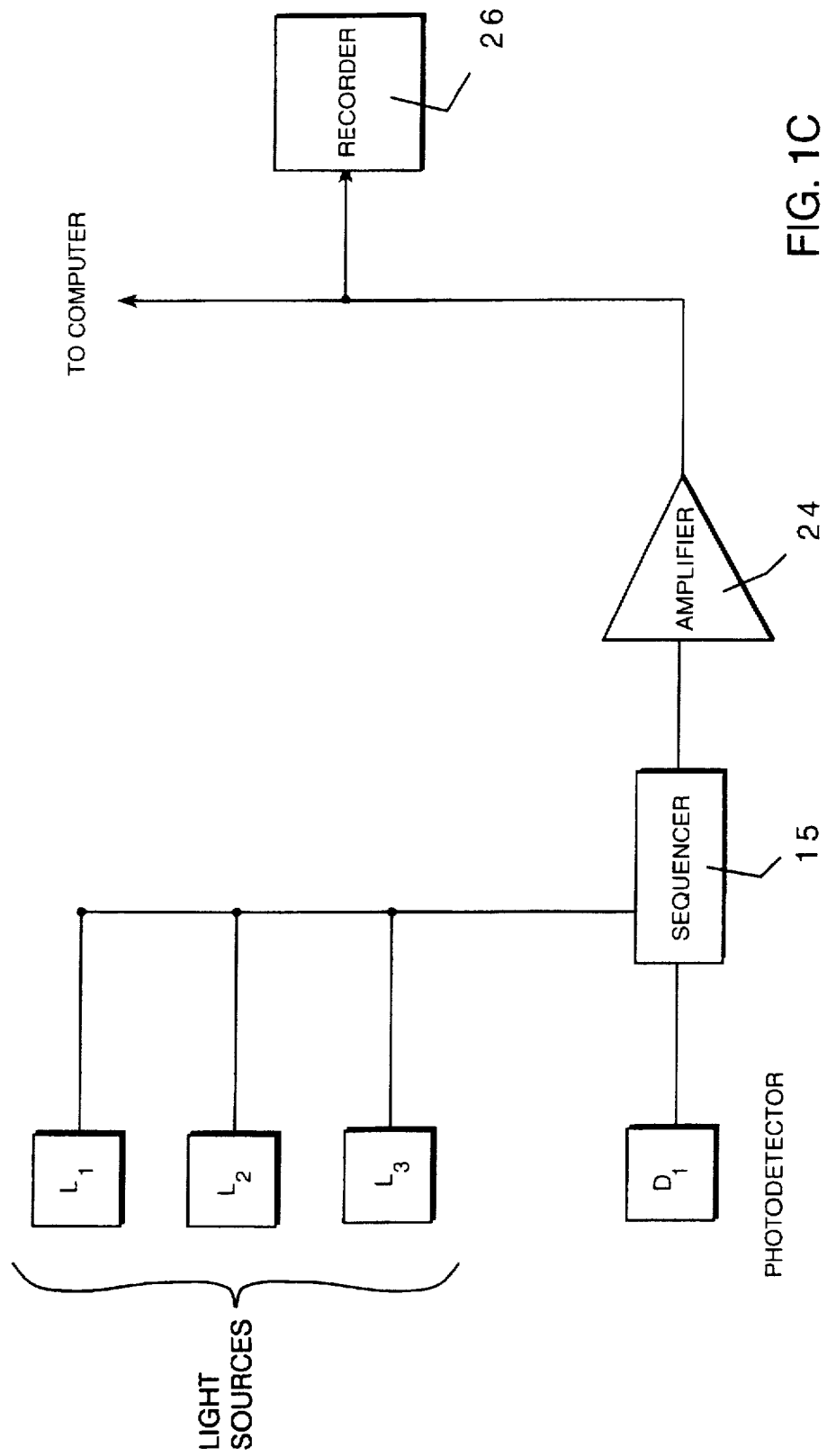
FIG. 1C is a block diagram of the monitor of FIG. 1.

As shown in FIGS. 1B and 1C, light received by detector $D_1$ first passes through an interference filter 22 having a passband corresponding to a wavelength of 850 nm. In the presently preferred embodiment, the interference filter is manufactured by Omega, Inc., and the silicon photodiode beneath it is Part No. F1227-66BR, available from Hamamatsu, having a large sensitive area for favorable signal to noise ratio and an NIR wavelength sensitivity. The sensitive area of the photodiode is approximately 6 mm². The silicon diode detector is connected to an amplifier 24 that is connected to a recorder 26 to give an intensity trace 28 as a function of time representative of the signals passing through a region of the patient's arm from the three light sources. Amplifier 24 drives the recorder with provision for offset of the zero point by adjustment of a potentiometer 25.

The three light sources are sequenced between the three sources at 20 sec. for each one. Light sequencer 15 contains three rheostats, which are adjusted to equalize the signals from the three lamps to give equal signal to noise ratios. The sequencer also contains three LED's 36, 38, 40 to indicate which lamp is sequenced. The sequencer applies not only the sequences to the three lamps but also flashes each light source on and off every half second so that a sample and hold circuit can monitor the difference between the light and dark signals. In this way, a stability of approximately $1 \times 10^{-5}$ optical density (OD) and a noise level of 0.1 of this is obtained with a response time of 1-2 seconds. In one embodiment, sequencer 15 is an independent source for determining the frequency of lamp flashing. Lamps flash at frequency of ½ Hz or 2 flashes per second or greater. In operation, one lamp flashes, the signal is picked up by the photodetector and while the lamp is on the intensity is measured and stored on the chart recorder or in computer memory.

All the data is acquired and compared with a chart recorder 26, and the zero value established with the light-off condition. The output of amplifier 24 may alternatively be sent to an electronic display unit (e.g., an LCD display). The analog signal from amplifier 24 may be digitized in the display unit and displayed as a digital number. The signal is also sent to a comparator (e.g., a computer) for comparing the measured light intensities from different source-detector positions against a predetermined calibration scale to provide a measure of solute concentration.

The three rheostats are adjusted to ensure that the signal intensities detected from the three light sources are equal during a calibration mode, described below. Thus, abscissa of the plots shown herein correspond to the base line obtained for the scatterer only condition (i.e., equal signals from all 3 light sources). The signal obtained during the calibration mode is termed $I_0$. The recorder gain may be increased to a desired level to obtain a desired sensitivity level, e.g., by factors of 2, 5, or 10. The measured signals are multiplied by this factor (i.e., 200, 500, 1000). Deflections of the three signals caused by changes in solute concentration are calculated as a percentage of the initial value ($I_0$) and multiplied by 0.00434 to convert to $\log_{10}$ for absorbency changes of less than 10% ($\Delta$OD). Otherwise, $\log_{10}$ is computed.

Figure 1D:
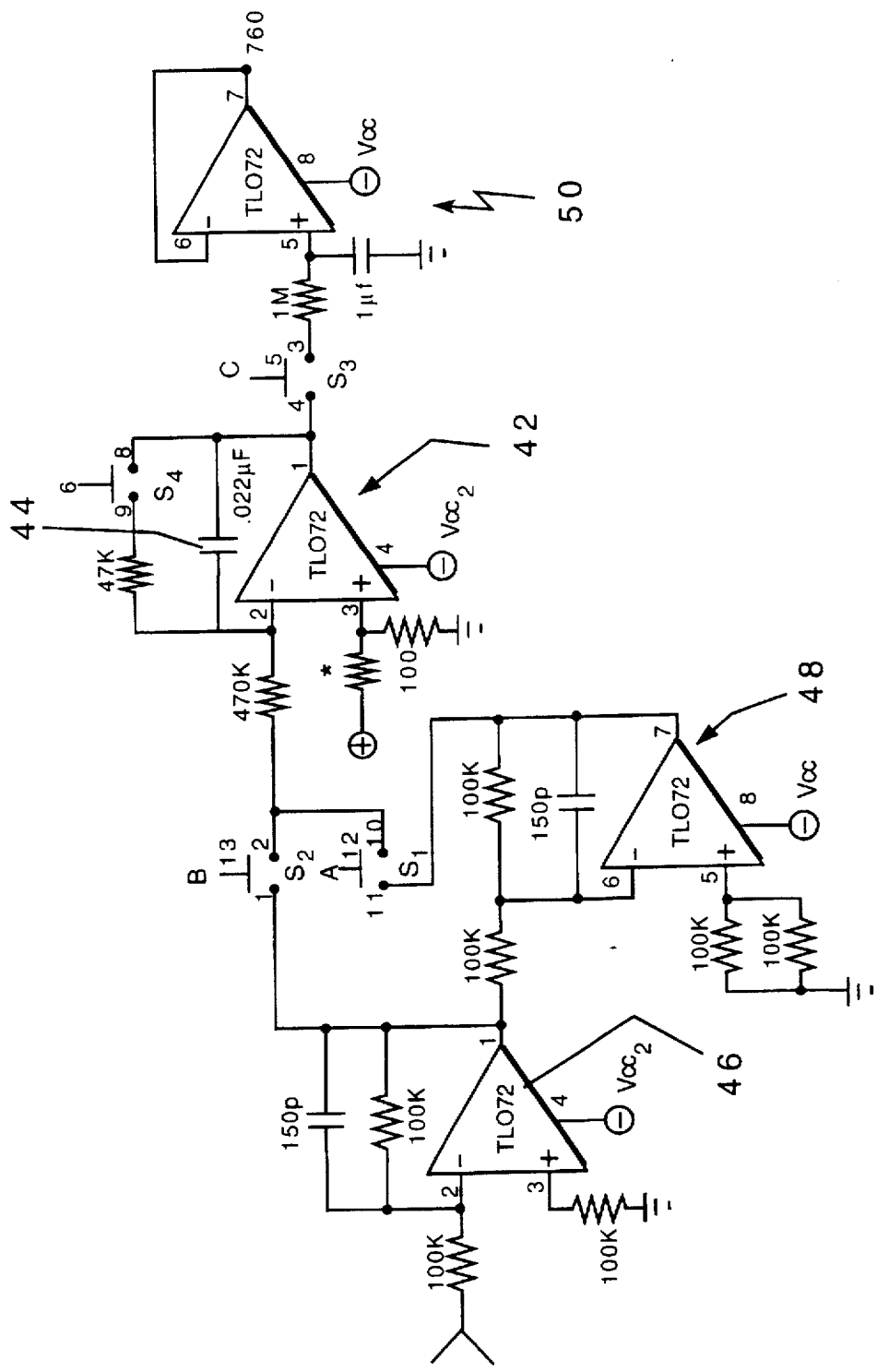
FIG. 1D is a schematic diagram of a circuit corresponding to a section of a sequencer.

Referring to FIG. 1D, sequencer 15 enables correction for the dark current/noise that comprises background light, DC offset of the operational amplifiers, photodiode dark current, temperature effects on the outputs of individual components and variations due to changing environment. The dark current/noise correction is explained in connection with a circuit 40. Monitor 10 performs data acquisition in four steps which are synchronized by the sequencer. In the first step, the lamps are off. The output of the detector is directed to an integrator 42 and an integration capacitor 44 is charged to the dark level voltage. In the second step, one of the lamps is turned on. The preamplifier output that corresponds to the intensity of the detected light is directed to integrator 42 in a way to charge capacitor 44 with current of polarity opposite to the polarity of the charging current in the first step. This is achieved using appropriate ON/OFF combination of switches S1 and S2. The voltage of capacitor 44 is charging to a value which, at the end of this step, represents the total signal minus the dark level noise signal. In the third step, both switches S1 and S2 are turned OFF to disconnect both the positive unity gain and the negative unity gain operational amplifiers (46 and 48). Then, the output of integrator 42 is moved via switch S3 to a hold circuit 50 which also functions as a low pass filter. This output is the detected signal corrected for the background noise. In the fourth step, the switches S1, S2 and S3 are open and switch S4 is closed in order to discharge capacitor 156 through a 47 K resistor. At this point, the circuit of integrator 154 is reset to zero and ready for the first step to be applied to the next lamp in the sequence.

In an alternative embodiment, the RUNMAN™ system described in International Publication No. WO 92/20273, filed May 18, 1992, which is herein incorporated by reference, may be used to detect the lamp signals migrating through the biological system. In this embodiment, the RUNMAN™ system is configured as described above and modified for single wavelength measurement (e.g., 850 nm).

As shown in FIGS. 2–2B, the measured results are plotted as optical density (OD) as a function of light source separation ($\rho_1$, $\rho_2$ and $\rho_3$). The OD is defined as $$OD = \log\left(\frac{I_0}{I}\right) \quad (1)$$

where, $I_0$ is the calibrated initial intensity and I is the detected intensity, which varies over time in this example as shown in FIG. 2. The plots of OD versus $\rho$ are linear for values of intralipid up to 1% (as discussed in detail below) and may show a non-linearity above that value for the largest detector light-source separation. In such a case, the smaller separations are used.

The best straight line or computer fit (e.g., by minimizing least mean square error) to the three data points for each measurement period ($T_0$, $T_1$) gives the slope in OD per solute concentration (usually 1 millimolar), and the extrapolation of the line to the ordinate gives the intercept. In some cases, a two-point slope is calculated (e.g., when only two sources are used, or when a data point corresponding to the largest source-detector spacing is subject to severe nonlinearity).

Similar plots of the variation of slope and intercept with solute and scatterer concentration are made, from which the final measures, namely OD per millimole solute per percent intralipid or per degree C are computed (as described in detail below). This gives the sensitivity parameter employed in this study.

Theory

According to diffusion theory, the intensity of continuous light remitted through a semi-infinite scattering medium, such as tissue, depends on the tissue absorption and scattering properties ($\mu_a$ and $\mu_s'$). The detected signal I($\rho$), at a separation of p from the source can be given as $$I(\rho) = \frac{1}{4\pi\mu_s'} \left[ \left(\mu_{\text{eff}} + \frac{1}{r_1}\right) \frac{e^{-\mu_{\text{eff}} r_1}}{r_1^2} + \left(\frac{4}{3}A + 1\right)\left(\mu_{\text{eff}} + \frac{1}{r_2}\right) \frac{e^{-\mu_{\text{eff}} r_1}}{r_2^2} \right] \quad (2)$$

where $$r_1 = \sqrt{\left(-\frac{1}{\mu_t'}\right)^2 + \rho^2}, \quad r_2 = \sqrt{\left(\frac{\frac{4}{3}A+1}{\mu_t'}\right)^2 + \rho^2},$$

$$\mu_t' = \mu_a + \mu_s', \quad \mu_{\mathit{eff}} = \sqrt{3\mu_a(\mu_a + \mu_s')},$$

and A is a parameter dependent upon the refractive index of the tissue and the initial light source intensity. When the source detector separation is larger than 2 cm, this equation can be simplified as $$I(\rho) = \frac{1}{a\mu_t'}\left(\mu_{\mathit{eff}} + \frac{1}{\rho}\right)\frac{e^{-\mu_{\mathit{eff}}\rho}}{\rho^2} \tag{3}$$

where $$a = \frac{4\pi}{2 + \frac{4}{3}A}$$

is a constant.

Taking logarithm of eq. (2) results in $$\ln[\rho^2 I(\rho)] = -\mu_{\mathit{eff}}\rho - \ln[a\mu_t'] + \ln\left[\mu_{\mathit{eff}} + \frac{1}{\rho}\right] \tag{4}$$

By having a calibration model with known values of $\mu_a(cal)$ and $\mu_s'(cal)$, we can compare an unknown sample to it, based on $$\ln[\rho^2 I_0(\rho)] - \ln[\rho^2 I(\rho)] = \tag{5}$$

$$\rho[\mu_{\mathit{eff}} - \mu_{\mathit{eff}}(cal)] + \ln\left[\frac{\mu_t'}{\mu_t'(cal)}\right] + \ln\left[\frac{\mu_{\mathit{eff}}(cal) + 1/\rho}{\mu_{\mathit{eff}} + 1/\rho}\right]$$

If the unknown and calibration samples have a small difference in optical properties, the last term of Eq. (5) can be negligible. Therefore, we can define the optical density such that $$OD = \log\left(\frac{I_0}{I}\right) = m\cdot\rho + b \tag{6}$$

where m is the slope and b is the intercept of the OD versus ρ line, given by:

$$m = \sqrt{3}\left(\sqrt{\mu_a\mu_s'} - \sqrt{\mu_a(cal)\mu_s'(cal)}\right) \tag{7}$$

$$b = \log\left(\frac{\mu_a + \mu_s'}{\mu_a(cal) + \mu_s'(cal)}\right)$$

where $\mu_a(cal)$ and $\mu_s'(cal)$ are the absorption and reduced scattering coefficients of the calibrated sample and $\mu_a$ and $\mu_s'$ are the absorption and reduced scattering coefficients of the sample to be monitored. By measuring OD versus the source detector separation, we can obtain slope (m) and intercept values (b). With the measured values of slope and intercept, we can obtain values for $\mu_a$ and $\mu_s'$ by solving Eq. 7 as follows.

$$\mu_a = \frac{1}{2}\cdot(y - \sqrt{y^2 - 4x}) \tag{8}$$

$$\mu_s' = \frac{1}{2}\cdot(y + \sqrt{y^2 - 4x})$$

where, $$x = \mu_a\mu_s' = \left[\frac{m}{\sqrt{3}} + \sqrt{\mu_a(cal) + \mu_s'(cal)}\right]^2 \tag{9}$$

$$y = \mu_a + \mu_s' = [\mu_a(cal) + \mu_s'(cal)]\,10^b$$

Eq. (6) exhibits a linear relationship between OD and the source-detector separation (ρ). The slope and intercept of this equation are studied here by measuring OD versus ρ.

Figure 3:
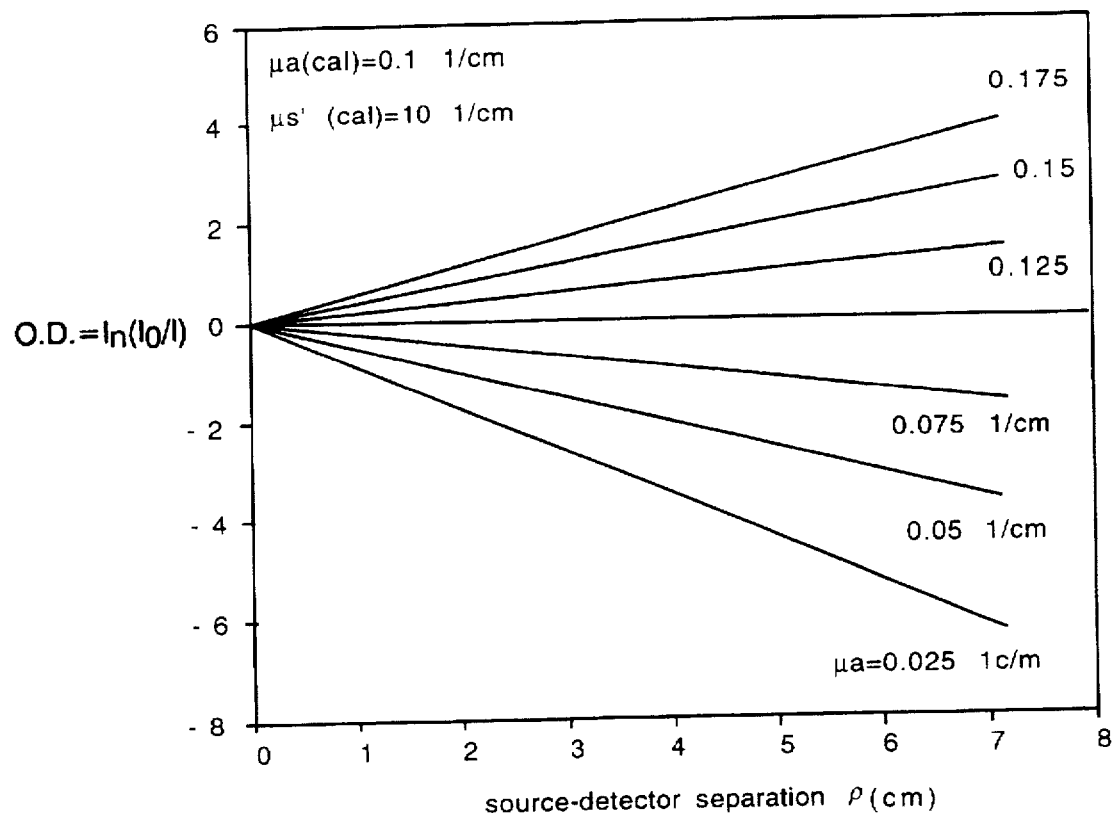
FIG. 3 is a plot of a calculated variation of the absorption coefficient ($\mu_a$) as a function of source-detector separation ($\rho$).

FIG. 3 shows a calculated result of OD versus source-detector separation as a function of absorption change of the measured sample. The calibration sample used here has $\mu_a(cal)$ and $\mu_s'(cal)$ values of 0.1 cm$^{-1}$ and 10 cm$^{-1}$, respectively, indicated by the standard horizontal line in the figure.

Figure 3A:
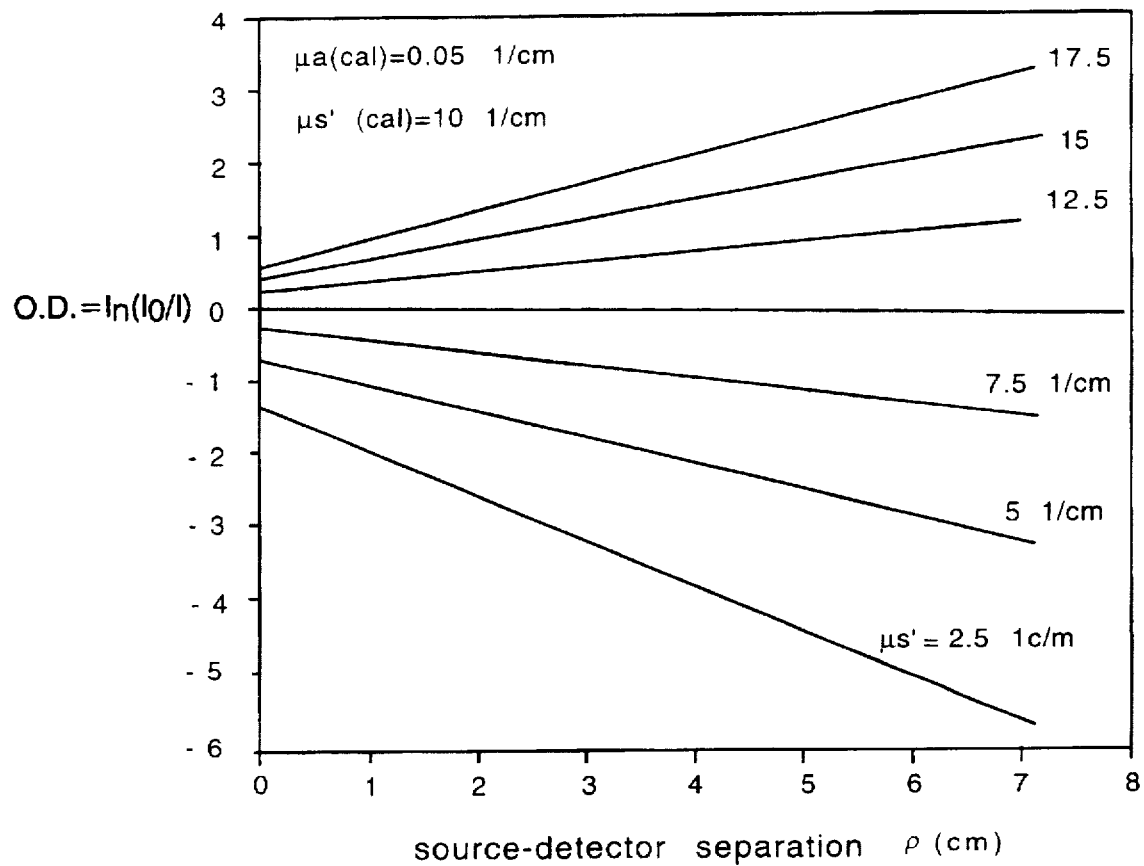
FIG. 3A is a plot of a calculated variation of the scattering coefficient ($\mu_s'$) as a function of source-detector separation ($\rho$).

FIG. 3A gives the slope and intercept dependence on the scattering property of the measured sample for the same calibrations. Above $\mu_s'=10$ cm$^{-1}$, the slope and intercept are of equal sensitivity, while the intercept is more sensitive below $\mu_s'=10$ cm$^{-1}$. FIG. 3A shows that the slope and intercept are negative if $\mu_s$ (sample)<$\mu_s'(cal)$, and the slope and intercept are positive if either $\mu_s$(sample)>$\mu_a(cal)$. Therefore, by determining the slope and intercept of OD versus source-detector separation, one can characterize the absorption and scattering properties or changes of an unknown sample with respect to the calibration sample, i.e., a relative $\mu_a\mu_s'$ is determined, as contrasted to frequency-domain or time-domain studies.

Figure 4:
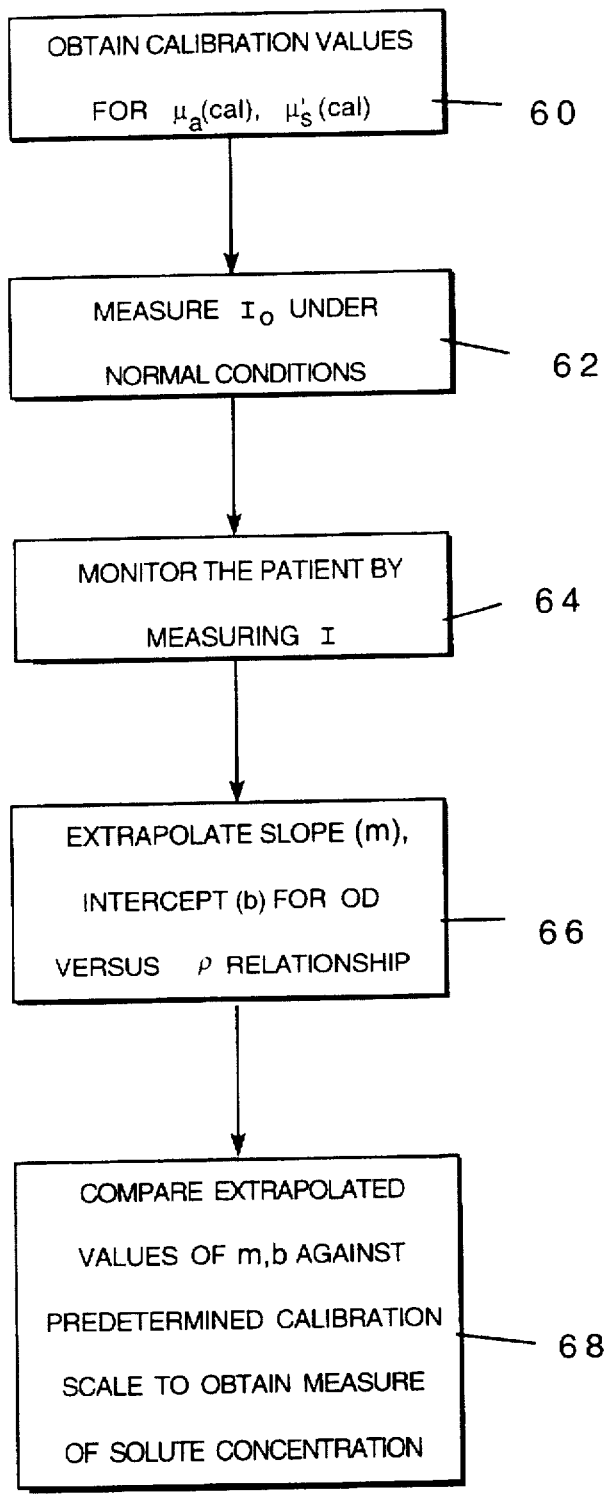
FIG. 4 is a flow diagram of a method for monitoring solute concentration.

Referring to FIG. 4, the concentration of one or more solutes in a biological system, e.g., a patient, may be monitored by the following process. Obtain calibration values $\mu_a(cal)$ and $\mu_s'(cal)$ corresponding to the intrinsic absorption and reduced scattering coefficients for a patient (step 60). These calibration values may be obtained using well known optical techniques (e.g., TRS or PMS) and need only be determined once for a given patient. These calibration values vary from patient to patient due to variations in skin pigmentation, variations in thicknesses of different skin layers, etc. Measure the so-called initial intensity $I_0$ for the patient under conditions that will be considered reference conditions (e.g., when the patient's biological systems are operating normally) (step 62). This initial intensity is used as the reference intensity for determining the determined optical density (OD; Eq. 1). Monitor the concentrations of one or more solutes in the patient by measuring the intensity (I) detected by the system described above for at least two different source-detector spacings (ρ) (step 64). The intensity (I) can then be used to determine a best linear fit to the at least two (OD, ρ) data points. Extrapolate slope (m) and intercept (b) values from the measured (OD, ρ) data points (step 66). Compare the extrapolated slope (m) and intercept (b) values against a predetermined calibration scale (e.g., as described below) to obtain a measure of solute concentration (step 68).

This monitoring process is preferably implemented in hardware (e.g., an ASIC) or as a software program run on a computer or other processor.

Calibration Scale

A calibration scale for relating the slope and intercept data monitored using the above-described technique to obtain a measure of one or more solute concentrations can be derived from measurements of a simulated biological environment or actual biological tissue.

EXAMPLE 1

Figure 5A:
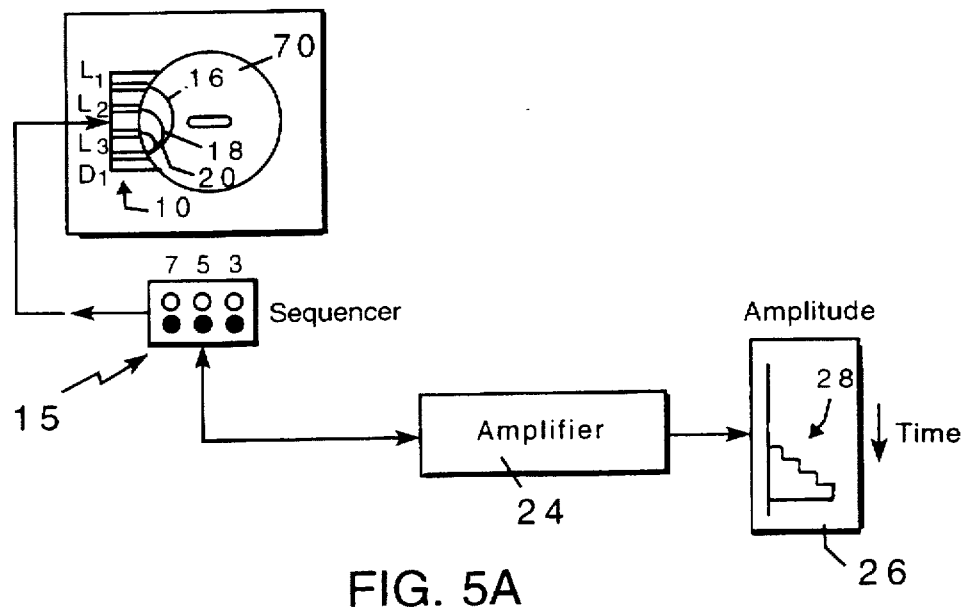
FIGS. 5 and 5A are diagrammatic side views of a calibration model and a monitor used for obtaining a calibration scale, respectively.
Figure 5:
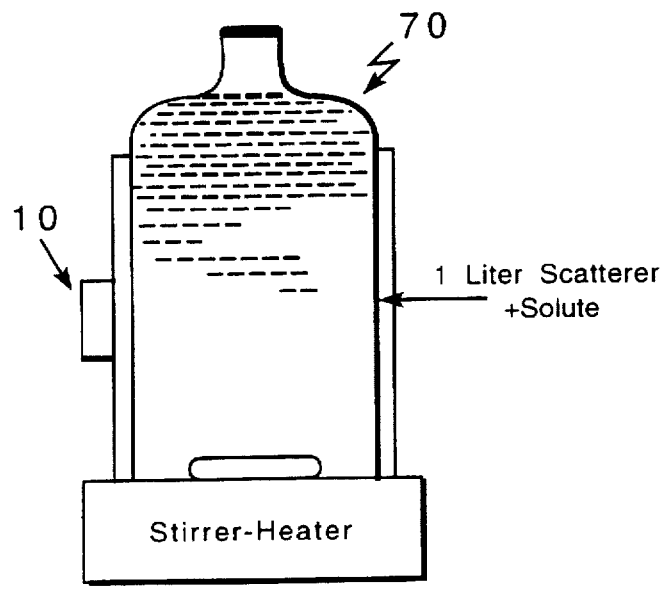

The layout of the components is illustrated in FIGS. 5 and 5A, which shows the tissue model as a 10 cm diameter cylinder 70 filled with one liter of a scatterer (e.g., intralipid). The slopes and intercepts are computed per 1% scatterer per millimolar (mM) solute per cm input/output at 25° (see FIG. 6).

In order to simulate the detection of solute in a breast, brain, or other portion of the human body, we have employed a cylindrical vessel of 10 cm in diameter and 10 cm in height, to which the optical detector is attached. The vessel is filled with distilled water to which appropriate concentrations of scatterer, for example, intralipid (0.1–2% by volume) are added. The vessel filled with a scattering medium with no solute present may be used as the calibration standard for $\mu_a$ and $\mu_s'$. The solute is then added in increasing concentrations as solid or liquid and dissolved or mixed appropriately by the rapid motion of the stirrer bar. Dilution of the scatterer is measured by dilatometry. Thus, relationships between absorbency changes due to the solute and scatterer concentrations are obtained.

Figure 7:
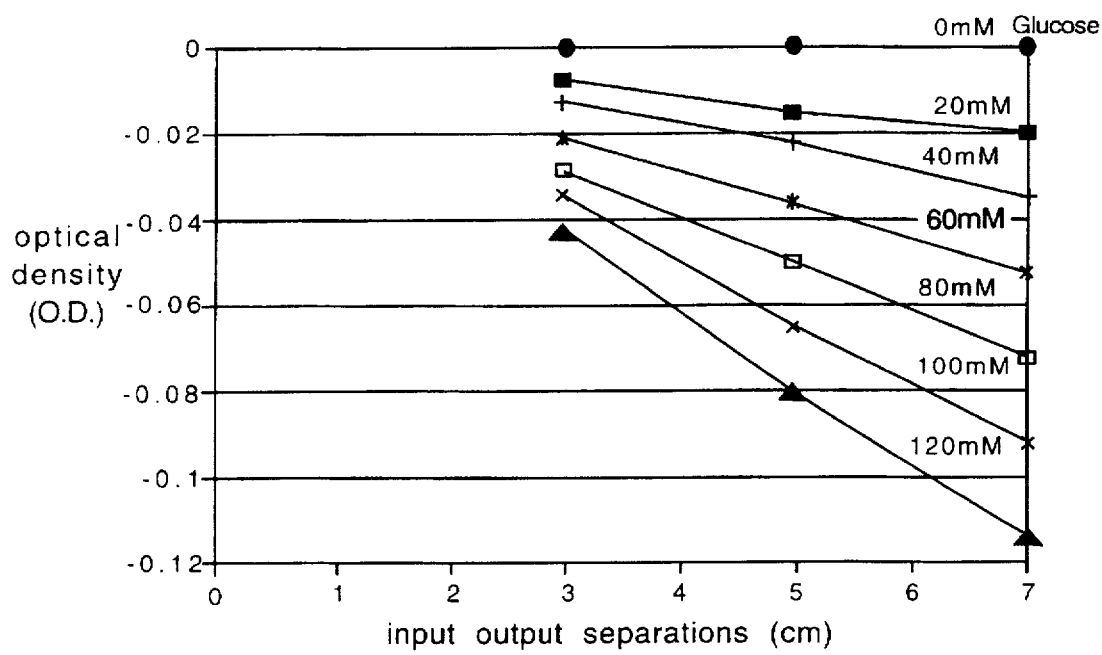
FIG. 7 is a plot of optical density (OD) as a function of input-output separation ($\rho$).

FIG. 7 illustrates the results of a typical experiment in 1% intralipid as a scatterer with solute additions of 10, 50, 100, etc. grams of glucose to 1 liter of 1% intralipid. OD decreases as a function of $\rho$, for 20 mM increments of glucose; both the slope and the intercept are affected. The errors due to instrument noise are approximately $1 \times 10^{-5}$ OD as compared with the 120 milli-OD scale of the data shown here. In this case an approximately linear relationship of OD and $\rho$ are obtained according to Eqs. 6 and 7.

Figure 7A:
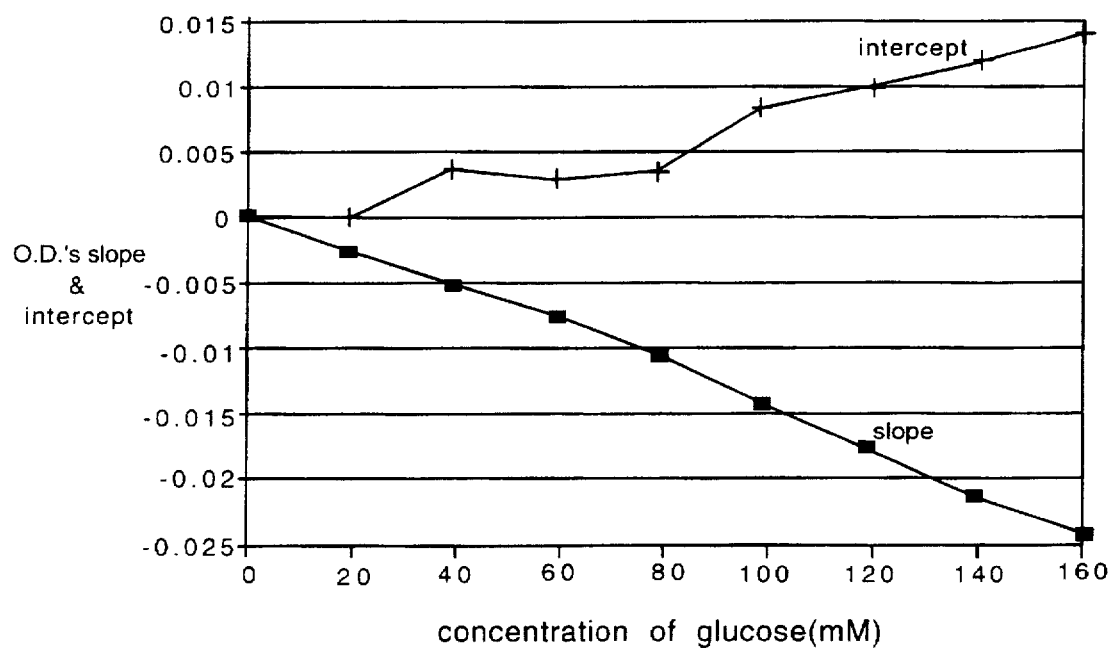
FIG. 7A is a plot of the slope and intercept extrapolated from the plot of FIG. 7 as a function of glucose concentration.

The relation between solute concentration, slope, and intercept (replotted from FIG. 7) is given in FIG. 7A, and the values are given in Table 1; slope and intercept values show $1.5 \times 10^{-4}$ OD and $0.91 \times 10^{-4}$ OD per mM of glucose and a 1 cm separation of input/output for slope.

These obtained values of slope and intercept are used either alone or in combination to provide a calibration scale against which subsequent measurements are compared to obtain a measure of solute concentration.

The values of slope are negative as indicated by FIGS. 7 and 7A, and for 1% intralipid a value of $-1.56 \pm 0.037$ is given (FIG. 6). The units are $10^{-4}$ OD per 1 mM glucose per 1 cm separation. The error of the slope is 0.037, and thus, the signal-to-error ratio in the determination of 1 mM glucose would from these data appear to be approximately 50 at 1 cm separation and correspondingly less at $\rho=7$ cm. It is noted that the appropriate coefficient of Eqs. 6 and 7 involves the square root of concentration.

The sensitivity, however, varies with the scatterer concentration, and thus the experiment has been repeated from 0.1%–1.5% of intralipid, and a new sensitivity constant, reduced to 1% scatterer concentration, is given in FIG. 6 (Table I) to be $1.56 \times 10^{-4}$ OD per 1 mM glucose per 1 cm separation per 1% intralipid. The square root relationship of Eqs. 6 and 7 is followed from 20 to 100 mM glucose, and the intercept follows a logarithmic relationship with a value of $90 \times 10^{-4}$ OD per cm per In 1 mM glucose. The values of the intercept increase with increasing intralipid $1.4 + 0.3 \times 10^{-4}$ OD/cm/1 mM glucose per intralipid %.

To monitor temperature variations, the vessel containing a solute (e.g., glucose) and scatterer (e.g., intralipid) is chilled to 20°, and the temperature is slowly ramped to 35° by an electric hotplate (upon rapid stirring) and the optical effects are recorded. The scatterer is stirred by a magnetic bar, and the temperature is regulated by the heater/thermostat so that temperatures between 20° and 30° can be employed. The temperature of the system is measured by a mercury thermometer.

EXAMPLE 2

Male SD strain rats, weighing 250–300 g. were used. After anesthetizing a rat by intraperitoneal injection pentobarbital (50 mg/kg weight), the liver was removed and perfused by Krebs-Ringer buffer containing 2 mM glucose. The buffer was oxygenated by the gas mixture 95% oxygen and 5% carbon dioxide. The liver was placed on an array of light sources and a detector with the separation of 1–3.3 cm. After liver perfusion became stable (20–30 minutes), the perfusate was changed to others containing different concentrations of glucose or mannitol. The oxygen concentration of outflow was simultaneously measured.

Precautions are necessary to ensure that the variations of the optical properties of the liver itself do not cause optical artifacts. Thus, the perfusion with solute is preceded and followed by control intervals. The lobes of the rat liver are laid upon an array of light sources and detectors similar to that indicated in FIGS. 1–1D, but with spacings of 1, 2 and 3 cm to account for the higher absorbance of the liver and the smaller size of the liver. Furthermore, the thickness of the lobe is approximately 2 cm and the tissue boundary conditions differ from the model of FIGS. 5 and 5A. We have chosen mannitol as the appropriate solute as contrasted to glucose in view of its negligible metabolic activity.

Figure 8:
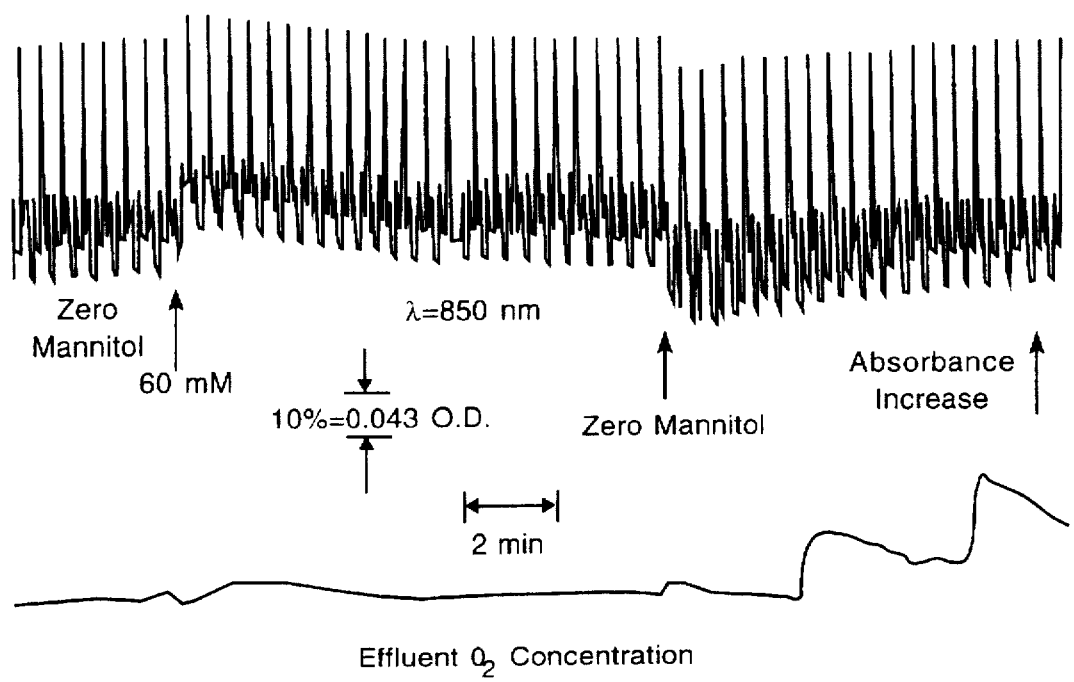
FIG. 8 is a schematic plot of the time course of a solute addition to the perfusate of rat liver.

A typical trace for the perfusion with 60 mM mannitol is shown in FIG. 8. The initial phase of absorbance increase is attributed to the entry of the mannitol into the sinusoids of the liver creating osmotic gradient, which equilibrates over the next 5 minutes. Thereafter, the absorbance change is assumed to be due to the equilibration of the mannitol with liver hepatocytes. In order to ensure that no remnant effect on the liver has occurred, the perfusate without solute is restored; the liver is reperfused with crystalloid in the absence of added mannitol. In this case, a decrease of absorbance occurs due to effusion of the mannitol from the tissue spaces, and thereafter the initial base line is restored. The mannitol effect is then measured as an early phase and a late phase, with respect to the two control levels.

Figure 8A:
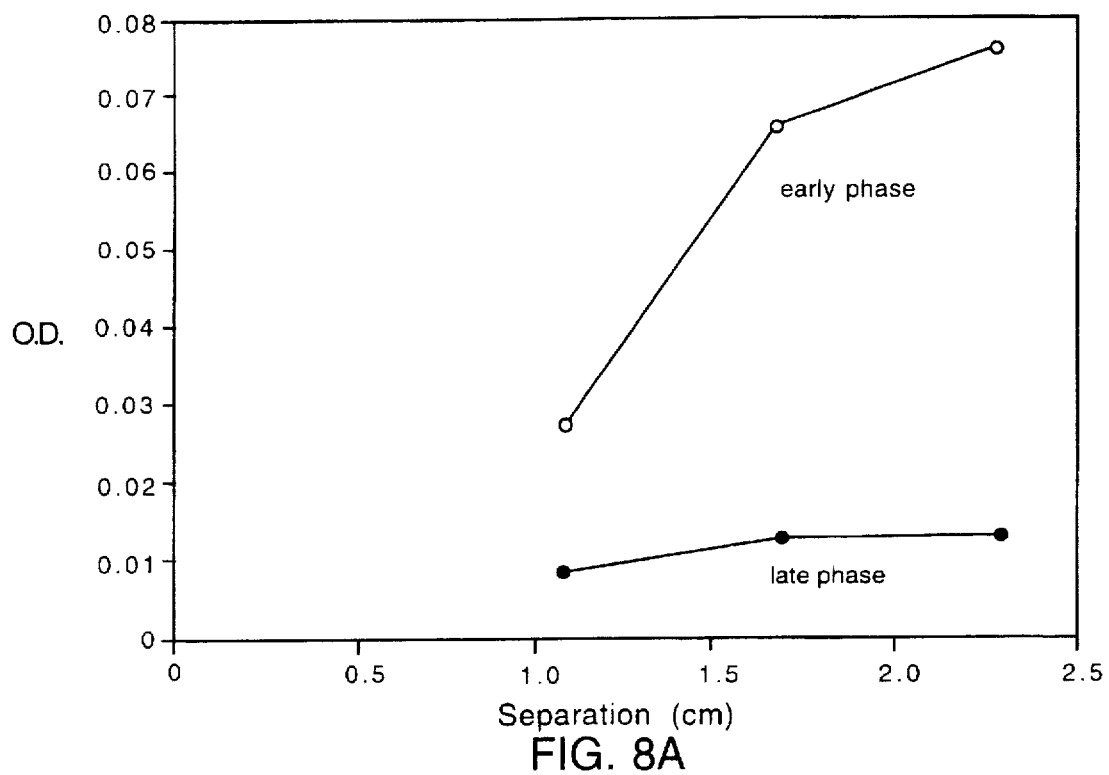
FIG. 8A is a plot of optical density (OD) as a function of input-output separation ($\rho$) illustrating the effect of mannitol upon the absorption of perfused liver (37° C.).
Figure 8B:
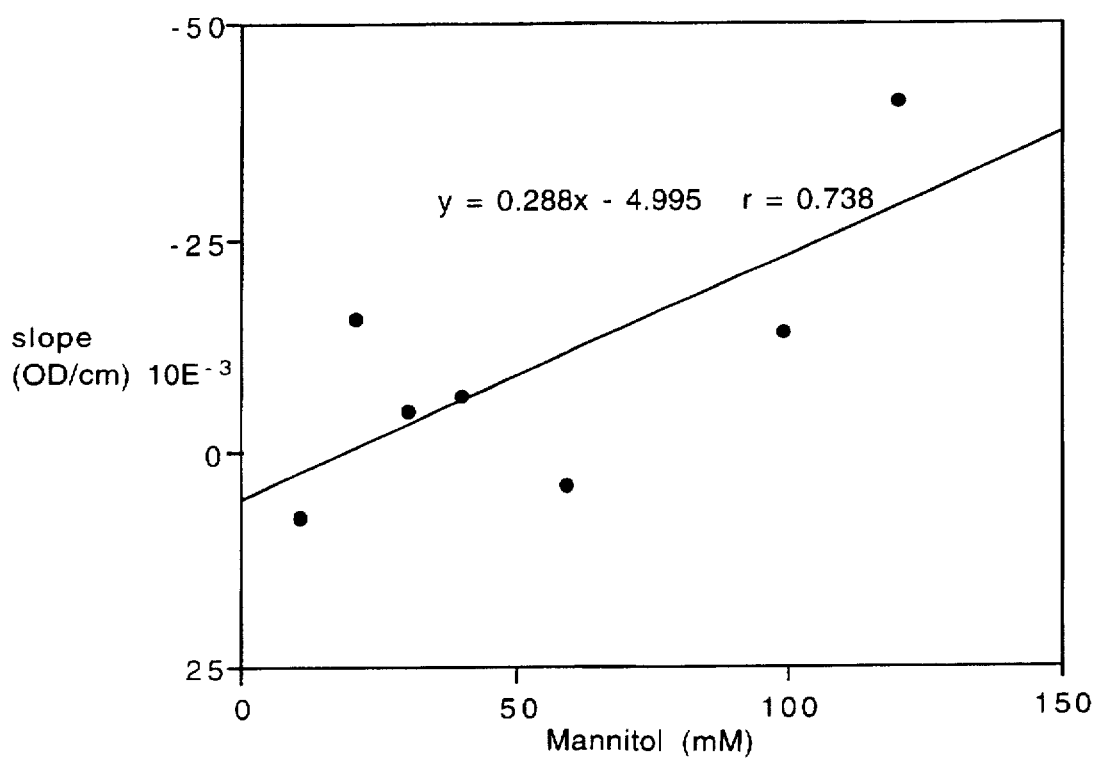
FIG. 8B is a plot of the slope of the OD plot of FIG. 8 as a function of mannitol concentration.

As shown in FIG. 8A, OD versus $\rho$ plots are obtained. These are much "noisier" than the intralipid and yeast cell models, probably due to osmotic and perfusion pressure effects. First, the sign of the early and late phases is similar. The slope of the early phase corresponds to a $+18 \times 10^{-4}$ OD per one mM of mannitol per cm separation of input/output. The late phase corresponds to $_+1.7 \times 10^{-4}$ OD per mannitol per cm.

Applications

Various solute concentrations may be monitored using the monitoring scheme of the present invention.

EXAMPLE I

The present invention provides is simple, cost-effective, portable scheme for monitoring the concentration of sugars (mannitol, fructose, sucrose, glucose) in a patient. Sensitivities of $1 \times 10^{-4}$ $_{66}$ OD per milliMole per percent intralipid at 25° have been observed. A comparison with a typical noise level of $10^{-5}$ $_A$OD, suggests that the range of 8–12 milli-Molar can be detected satisfactorily.

The glucose concentration in a patient is monitoring according to this example by attaching the monitor of FIGS. 1–1D to the patient on the breast, the belly, the finger, or on the head. The optimum tissue for this determination is one in which the extravascular glucose level is rapidly equilibrated with the blood vessels.

Figure 9:
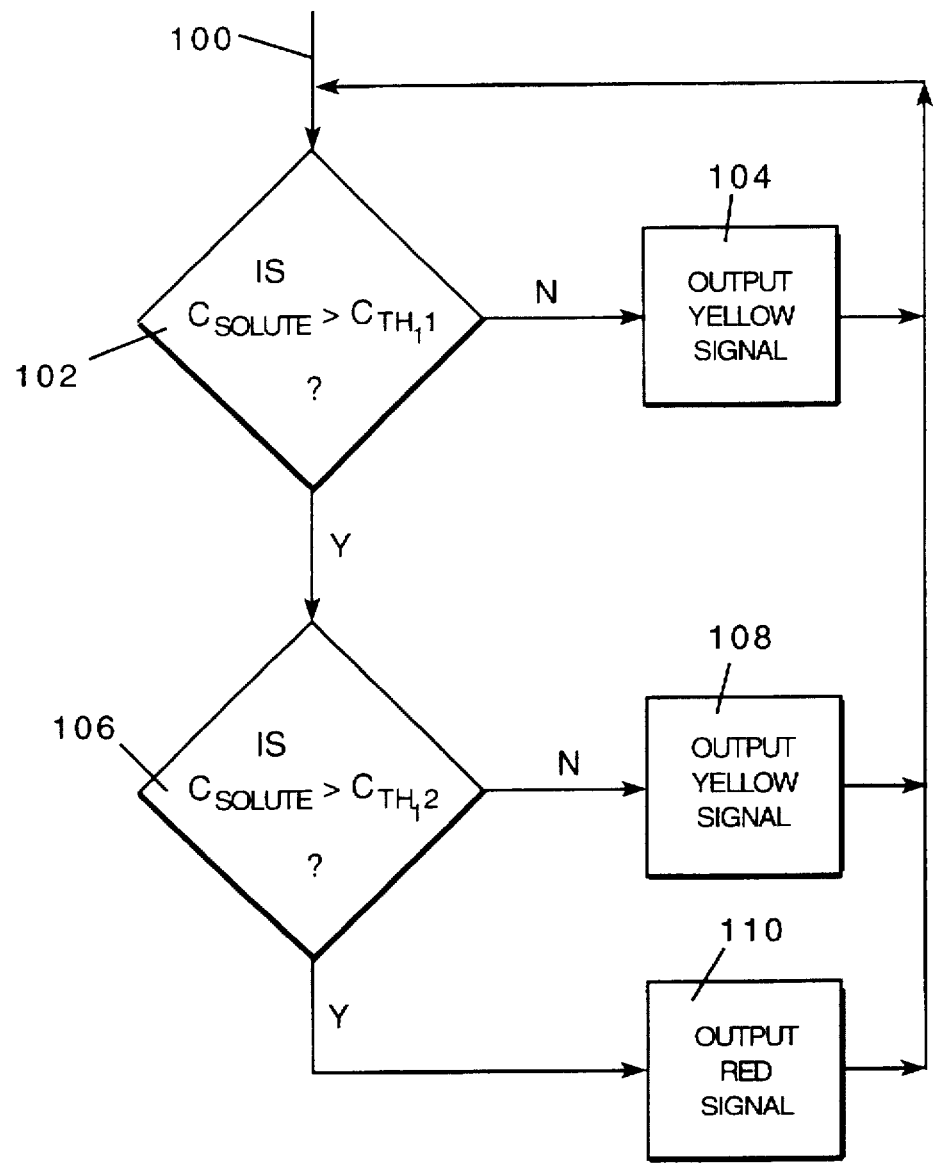
FIG. 9 is a flow diagram of a scheme for indicating to a patient measured solute concentration.

Referring to FIG. 9, in one preferred embodiment of a glucose monitor useful, e.g., for monitoring the glucose level of a diabetic patient, the patient's blood glucose concentration is detected using the process described above in connection with FIG. 4 (100). In one embodiment, the patient reads the extrapolated slope and intercept values directly from the output of a comparator (e.g., a computer or other processor) and compares these values to a predetermined calibration scale (described above).

In an alternative embodiment, a processor receives the extrapolated slope and intercept values and compares these values to a predetermined stored calibration scale. The processor further implements the following steps to indicate to the patient the measured solute concentration. If the measured concentration ($C_{solute}$) is less than a first predetermined threshold concentration ($C_{th,1}$), e.g., 0–100 mMol and more preferably 50 mMol (step 102), a green signal is output (104), e.g., by lighting a green light, indicating the patient's blood glucose level is generally within normal levels. If the measured concentration is greater than $C_{th,1}$, the measured concentration is compared against a second predetermined threshold concentration ($C_{th,2}$), e.g., 50–200 mMol and more preferably 120 mmol (step 106). If $C_{solute}$ is less than this second threshold concentration, a yellow signal is output (108), indicating that the patient's blood glucose level has risen above normal levels and should be monitored carefully. If $C_{solute}$ is greater than $C_{th,2}$, a red signal is output (110), indicating that the patient should attempt to remedy his or her condition.

EXAMPLE II

The alcohol concentration in a patient may also be monitored using the scheme according to the present invention. Ethanol readily equilibrates with tissue spaces and gives a relatively small but significant signal. Accordingly, a patient (as used herein the term "patient" is used to broadly refer to a person in general whether or not the person is being treated for a medical problem) attaches the monitor of FIGS. 1–1D to the breast, the belly, the finger, or the head. A processor, as described above in connection with Example I receives as input light intensity signals from a monitor as described in connection with FIGS. 1–1D and implements the algorithms shown in FIGS. 4 and 9 to provide a measure of the alcohol content in the patient's system.

The calibration scales are determined empirically as described above, e.g., in connection with Example 1. The threshold levels ($C_{th,1}$, $C_{th,2}$) are selected to correspond to desired criteria (e.g., legal drinking limit).

EXAMPLE III

The concentration of salts (e.g., NaCl, KCl and MOPS) in a patient may also be monitored using the scheme according to the present invention. Accordingly, a patient attaches the monitor of FIGS. 1–1D to the breast, the belly, the finger, or the head. A processor, as described above in connection with Example I receives as input light intensity signals from a monitor as described in connection with FIGS. 1–1D and implements the algorithms shown in FIGS. 4 and 9 to provide a measure of the alcohol content in the patient's system. FIG. 10 (Table II) includes data on NaCl, KCl, and MOPS. The effect of these electrolytes is relatively small but significant.

The calibration scales are determined empirically as described above, e.g., in connection with Example 1. The threshold levels ($C_{th,1}$, $C_{th,2}$) are selected to correspond to desired criteria, depending, e.g., on the health of the patient. For example, patient's with high blood pressure would be assigned lower threshold concentrations.

EXAMPLE IV

Enhanced results are achievable if the affects solute concentrations other than that which is to be measured can be ignored. According to this example, the history of the patient is well characterized so that it can be assumed that variations in the monitored concentration level are due to variations in the solute concentration that is desired to be measured.

For example, an enhanced glucose concentration measurement of a patient is obtained using the monitor described in FIGS. 1–1D, which is coupled to a processor for implementing the steps of FIG. 4, when the patient has not subjected himself or herself to elevated concentrations of other scattering solutes, such as alcohol and salts.

In view of the low specificity in solute discrimination, especially the physiologically important ones, glucose, ethanol, mannitol, and to a lesser extent NaCl and KCl, the in vivo studies are undertaken with supplementary information of the parenteral fluids in use. In addition, the osmotic transients and indeed the osmotic state of the tissue can be of importance, especially in patients undergoing dialysis procedures. Finally, and possibly most important, is the body tissue temperature, which should be monitored in the particular tissue volume studies optically, probably by the water absorption.

FIG. 11 (Table III) illustrates the effect of a variety of solutes, mannitol fructose, and propanediol in the range of molarities up to that indicated in the table. The slope is normalized in the same way as above, except it is not divided by the percent of intralipid. The slope values are within the experimental error equal to mannitol and fructose. Alcohols and propanediol give a significantly smaller slope per mM and a much smaller intercept after connection for dilution (see below). The small effect of methanol on yeast cells as a scatterer is noted in Table IV.

At the same time, an appropriate correction for water absorption may be implemented.

Furthermore, since intensity measurements are especially sensitive to changes in the skin contact between the probe and the phantom or the probe and the body tissue makes measurements which do not depend upon intensities vastly preferable, and one of these methods is the phase modulation system, which surely would be the ultimate system for most reliable measurements. However, the relationship between the intensity signal and the phase signal is such that very high phase sensitivities are required. The absorbance limitation of $10^{-5}$ may have to be measured, which requires similar accuracies of phase determination.

Other Embodiments

More than three sources may be used to obtain enhanced measurements by obtaining a greater number of data points from which to extract the linear parameters (slope and intercept).

Instead of using multiple light sources a single source may be used, which applies the light to the biological system from locations spaced from the detector by different distances. Alternatively, the single source may remain stationary and the detector may be sequentially moved to detecting positions located at different distances from the source.

We have observed that the monitoring scheme described herein has a relatively small wavelength dependence. Thus, a dual wavelength method may be used for this purpose for the minimization of hemoglobin crosstalk. In this technique the hemoglobin concentration is quantified by an appropriate phase modulation spectrophotometer to provide accurate path length information at the wavelengths involved. Thus, the discrepancy of absorbance measurements at 850 nm from the hemoglobin spectrum can be assumed to be counted as pertaining to the solute measurement.

Possible variability of the light entry into the tissue and its arrival at the detector system consisting of a silicon diode or a fiber coupler (e.g., due to variable tissue contact) may be compensated for by frequency-domain methods, which may have a significant advantage for tissue contact. The use of several input-output spacings is necessary for these determinations. The different spacings sample different tissue volumes of different depths: the short spacing—shallow and the long spacing—deep tissue volumes. Thus, in cases where heterogeneous tissue is involved, the possibility that different solute levels are sampled at different input-output spacings should be compensated for.

Time-domain methods may alternatively be used. These methods sample different tissue volumes for the calculation $\mu_s'$ and $\mu_a$ (early and late, respectively). The use of Fourier transformation from time to frequency domain may rectify this problem. In these frequency-domain devices, the high frequency waves penetrate shallowly and the low frequency deeply. Thus, dual measurements, particularly at a pair of wavelengths at which the absorption is canceled out, serve as useful means for calculating scattering factor.

Still other embodiments are within the scope of the claims.

For example, the TRS system described in U.S. Ser. No. 08/040,168, filed Mar. 30, 1993, and also described in Sevick et al., *Analytical Biochemistry*, Vol 195, pp. 330–351 (1991), which are both herein incorporated by reference may be used to measure the reduced scattering coefficient $\mu_s'$ and the absorption coefficient $\mu_a$. These values of the $\mu_s'$ and $\mu_a$ may then be used with the above-described technique to obtain a measure of a solute concentration (e.g., glucose concentration). Alternatively, the PMS system described in U.S. Ser. No. 08/031,945, filed Mar. 16, 1993, and also described in Sevick et al., *Analytical Biochemistry*, Vol 195, pp. 330–351 (1991), which are both herein incorporated by reference, operating at a wavelength selected between 1 GHz and 50 MHz, may be used to obtain a value for the reduced scattering coefficient $\mu_s'$ and the absorption coefficient $\mu_a$ which can be used with the technique described above to obtain a measure of a solute concentration (e.g., glucose concentration). The TRS and PMS systems described in these references may be operated at higher wavelengths (e.g., 1,000–1,500 nm), where the glucose is active, to determine the glucose concentration directly.

What is claimed is:

1. A method for in vivo monitoring one or more solutes in a biological system comprising the steps of:

delivering light from at least one light source of at least one wavelength into a biological system containing one or more solutes, said wavelength being in a range of visible or infrared light and exhibiting substantially no measurable absorption variation for said one or more solutes;

detecting by at least one light detector at least first and second intensity portions of said delivered light at said wavelength, said first portion having traveled through said biological system along photon migration paths characterized by a first average path length, and said second portion having traveled through said biological system along photon migration paths characterized by a second average path length that is greater than said first average path length;

adjusting by a control a relationship between said detected first and second intensity portions and said first and second average path lengths according to a known model thereby obtaining selected initial values of said first and second portions;

detecting over time said first and second intensity portions of said delivered light after said adjusting step;

comparing said detected first and second intensity portions to said initial values of said first and second portions, respectively, according to said model;

fitting to a linear model said first and second compared portions of the delivered light as a function of distances representative of said first and second average path lengths; and monitoring a measure of a concentration of one or more of said solutes in said biological system based on a parameter of said linear model.

2. The method of claim 1 wherein the step of delivering said light includes generating said light by said light source and irradiating said biological system from two input ports, and the step of detecting said first and second portions includes collecting said light at at least one detection port being optically connected to said detector.

3. The method of claim 2 wherein said parameter of said linear model is a slope.

4. The method of claim 2 wherein said parameter of said linear model is an intercept.

5. The method of claim 2 wherein said distances are at least three centimeters.

6. The method of claim 2 wherein said distances are selected to perform monitoring of said solute present in the liver.

7. The method of claim 1 further comprising the step of detecting a third portion of said delivered light, said third portion having traveled through said biological system along photon migration paths characterized by a third average path length that is greater than said first and second average path lengths.

8. The method of claim 1 further comprising the steps of:

delivering light of a second wavelength into said biological system containing one or more solutes, said second wavelength being in a range of visible or infrared light and exhibiting substantially no measurable absorption variation for said one or more solutes;

detecting at least first and second portions of said delivered light at said second wavelength, said first portion having traveled through said biological system along photon migration paths characterized by a first average path length of said second wavelength, and said second portion having traveled through said biological system along photon migration paths characterized by a second average path length of said second wavelength that is greater than said first average path length; and comparing, at said second wavelength, said first and second portions of the delivered light to monitor a concentration of one or more of said solutes in said biological system.

9. A method for in vivo monitoring one or more solutes in a biological system comprising the steps of:

delivering light from at least one light source of at least one wavelength into a biological system containing one or more solutes, said wavelength being in a range of visible or infrared light and exhibiting substantially no measurable absorption variation for said one or more solutes;

detecting by at least one detector at least first and second portions of said delivered light at said wavelength, said first portion having traveled through said biological system along photon migration paths characterized by a first average path length, and said second portion having traveled through said biological system along photon migration paths characterized by a second average path length that is greater than said first average path length;

adjusting by a control a relationship between said detected first and second portions of said delivered light and said first and second average path lengths according to a known model thereby obtaining selected initial values of said first and second portions;

detecting over time said first and second portions of the delivered light after said adjusting step;

comparing said detected first and second portions of the delivered light to said initial values of said first and second portions, respectively, according to said model; and monitoring a measure of a concentration of one or more of said solutes in said biological system based on said compared first and second portions.

10. The method of claim 9 wherein the step of monitoring said measure of a concentration of one or more of said solutes in said biological system includes employing a predetermined concentration scale.

11. The method of claim 9 wherein the step of monitoring said measure includes monitoring a variable proportional to, the scattering coefficient of said biological system.

12. A method for in vivo monitoring one or more solutes in a biological system comprising the steps of:

delivering light of at least one wavelength into a biological system containing one or more solutes, said wavelength being in a range of visible or infrared light and exhibiting substantially no measurable absorption variation for said one or more solutes;

measuring first and second reference intensities ($I_{1,ref}$, $I_{2,ref}$) corresponding to first and second portions of said delivered light at said wavelength, said first portion having traveled through said biological system along photon migration paths characterized by a first average path length, and said second portion having traveled through said biological system along photon migration paths characterized by a second average path length that is greater than said first average path length;

measuring first and second intensities ($I_1$, $I_2$) corresponding to first and second portions of said light delivered to said biological system after measuring said first and second reference intensities ($I_{1,ref}$, $I_{2,ref}$);

determining relative changes, over time, in said first and second intensities ($I_1$, $I_2$) relative to first and second reference intensities ($I_{1,ref}$, $I_{2,ref}$); and comparing said relative changes to monitor a concentration of one or more of said solutes in said biological system.

13. The method of claim 10 wherein said step of determining relative changes in said first and second intensities further comprises respectively determining first and second optical densities ($OD_1$, $OD_2$) wherein $$OD_1 = \log\left(\frac{I_1}{I_{1,ref}}\right)$$

and $$OD_2 = \log\left(\frac{I_2}{I_{2,ref}}\right).$$

14. The method of claim 13 wherein said step of comparing said first and second portions of the delivered light comprises using a linear model relating said first and second optical densities to distances ($\rho_1$, $\rho_2$) representative of said first and second average path lengths to obtain a characterization of said biological system representative of the concentration of one or more of said solutes in said biological system.

15. The method of claim 14 wherein the characterization that is obtained is a slope (m) determined by $$m = \frac{OD_2 - OD_1}{\rho_2 - \rho_1}.$$

16. The method of claim 14 wherein the characterization that is obtained is an intercept (b) determined by $$b = \frac{OD_1 \cdot \rho_2 - OD_2 \cdot \rho_1}{\rho_2 - \rho_1}.$$

17. A system for in vivo monitoring one or more solutes in a biological system comprising:

a source-detector arrangement formed by at least one light source constructed to deliver into a biological system light of a wavelength in a visible or infrared range, said wavelength exhibiting substantially no measurable absorption variation for one or more solutes present in said biological system, and at least one light detector constructed to detect light of said wavelength that has migrated in said biological system, said source-detector arrangement constructed to provide at least first and second detected portions of said delivered light, said first portion having traveled through said biological system along photon migration paths characterized by a first average path length, and said second portion having traveled through said biological system along photon migration paths characterized by a second average path length that is greater than said first average path length, a control constructed and arranged to adjust a relationship between said detected first and second intensity portions and said first and second average path lengths according to a known model thereby obtaining selected initial values of said first and second portions;

a comparator constructed and arranged to compare said detected first and second intensity portions to said initial values of said first and second portions, respectively, according to said model; and said comparator also constructed and arranged to fit to a linear model said compared first and second portions of the delivered light as a function of distances representative of said first and second average path lengths and to monitor a measure of a concentration of one or more of said solutes in said biological system based on a parameter of said linear model.

18. The system of claim 17 wherein said source-detector arrangement includes two light sources positioned at different distances relative to one light detector.

19. The system of claim 18 wherein said source-detector arrangement further includes a third light source and said arrangement further constructed to provide third portion of said delivered light, said third portion having traveled through said biological system along photon migration paths characterized by a third average path length that is greater than said first and second average path lengths.

20. The system of claim 17 wherein said source-detector arrangement includes one light source positioned at different distances relative to two light detectors.

21. The system of claim 20 wherein said source-detector arrangement further includes a third light detector and said

17 arrangement further constructed to provide third portion of said delivered light, said third portion having traveled through said biological system along photon migration paths characterized by a third average path length that is greater than said first and second average path lengths.

22. A method for in vivo monitoring one or more solutes in a biological system comprising the steps of:

generating a carrier waveform of a frequency on the order of $10^8$ Hz;

generating light of at least one wavelength, said wavelength being in a range of visible or infrared light and exhibiting substantially no measurable absorption variation for one or more solutes;

modulating said light by said carrier waveform prior to delivering said light into a biological system containing said one or more solutes;

detecting over time a first portion of said modulated light that has traveled in said biological system along photon migration paths characterized by a first average path length, and detecting over time a second portion of said modulated light that has traveled in said biological system along photon migration paths characterized by a second average path length that is greater than said first average path length;

measuring a first phase shift of said first detected portion of said modulated light relative to said delivered modulated light, measuring a second phase shift of said second detected portion of said modulated light relative to said delivered modulated light, and based upon said first and second phase shifts monitoring a measure of a concentration of said solute in said biological system.

23. The method of claim 22 wherein said monitoring said concentration of said solute includes calculating a scattering coefficient of said solute.

24. The method of claim 23 wherein said monitoring said concentration of said solute includes determining absolute concentration of said solute based on said calculated scattering coefficient.

25. A method for in vivo monitoring one or more solutes in a biological system comprising the steps of:

generating pulses of light of at least one wavelength having an input waveform of duration on the order of a nanosecond or less, said wavelength being in a range of visible or infrared light and exhibiting substantially no measurable absorption variation for one or more solutes;

delivering said pulses of light into a biological system containing said one or more solutes;

detecting over time a first pulse waveform of a first portion of light traveled in said biological system along photon migration paths characterized by a first average path length, and detecting over time a second pulse waveform of a second portion of light traveled in said biological system along photon migration paths characterized by a second average path length that is greater than a first average path length;

storing over time signals corresponding to said detected pulse waveforms, determining changes in shapes of said detected pulse waveforms, at said wavelength, relative to said input pulse waveform, and based upon said changes monitoring a measure of a concentration of said solute in said biological system.

18

26. The method of claim 25 wherein said monitoring said concentration of said solute includes calculating a scattering coefficient of said solute.

27. The method of claim 26 wherein said monitoring said concentration of said solute includes determining absolute concentration of said solute based on said calculated scattering coefficient.

28. The method of claim 1, 22 or 25 wherein said solute is one of the following: a low molecular weight carbohydrate, an alcohol, or an electrolyte.

29. The method of claim 28 wherein said solute is one of the following: mannitol, fructose, sucrose, glucose, propanediol, methanol, ethanol, sodium ion, potassium ion, and chloride ion.

30. The method of claim 1, 22 or 25 wherein said biological system includes one of the following: the finger, the arm, the head, the belly, and the liver.

31. A system for in vivo monitoring one or more solutes in a biological system comprising:

a source-detector arrangement formed by at least one light source constructed to deliver into a biological system light of a wavelength in a visible or infrared range, said wavelength exhibiting substantially no measurable absorption variation for one or more solutes present in said biological system, and at least one light detector constructed to detect light of said wavelength that has migrated in said biological system, an oscillator constructed to generate a first carrier waveform at a frequency on the order of $10^8$ Hz;

said light source being coupled to said oscillator and constructed to generate light of said wavelength modulated by said carrier waveform;

said detector constructed to detect over time a first portion of said modulated light that has traveled along photon migration paths characterized by a first average path length, and detect over time a second portion of said modulated light that has traveled along photon migration paths characterized by a second average path length that is greater than said first average path length;

a phase detector constructed to measure a first phase shift of said first detected portion of said modulated light relative to said delivered modulated light, and measure a second phase shift of said second detected portion of said modulated light relative to said delivered modulated light; and a comparator constructed to monitor, based upon said first and second phase shifts, a measure of a concentration of said solute in said biological system.

32. The system of claim 31 wherein said comparator is further constructed and arranged to calculate a scattering coefficient of said solute.

33. The system of claim 32 wherein said comparator is further constructed and arranged to determine absolute concentration of said solute based on said calculated scattering coefficient.

34. A system for in vivo monitoring one or more solutes in a biological system comprising:

a source-detector arrangement formed by at least one light source constructed to deliver into a biological system light of a wavelength in a visible or infrared range, said wavelength exhibiting substantially no measurable absorption variation for one or more solutes present in said biological system, and at least one light detector constructed to detect light of said wavelength that has migrated in said biological system.

a pulser constructed to generate pulses of an input waveform of duration on the order of a nanosecond or less;

said light source, receiving said pulse of said input waveform, constructed to introduce into said biological system pulses of said wavelength having said input waveform;

said detector constructed to detect over time a first pulse waveform of a first portion of light traveled along photon migration paths characterized by a first average path length, and detect over time a second pulse waveform of a second portion of light traveled along photon migration paths characterized by a second average path length that is greater than said first average path length;

an analyzer, connected to a comparator, constructed to store over time signals corresponding to said detected pulse waveforms; and said comparator constructed to determine changes in shapes of said detected pulse waveforms at said wavelength relative to said input pulse waveform, and based upon said changes monitor a concentration of said solute in said biological system.

35. The system of claim 34 wherein said comparator is further constructed and arranged to calculate a scattering coefficient of said solute.

36. The system of claim 35 wherein said comparator is further constructed and arranged to determine an absolute concentration of said solute based on said calculated scattering coefficient.

37. The system of claim 17, 31 or 34 wherein said source-detector arrangement is further constructed to deliver light of a second wavelength into said biological system containing one or more solutes, said second wavelength being in a range of visible or infrared light and exhibiting substantially no measurable absorption variation for said one or more solutes; and detect at least first and second portions of said delivered light at said second wavelength, said first portion having traveled through said biological system along photon migration paths characterized by a first average path length of said second wavelength, and said second portion having traveled through said biological system along photon migration paths characterized by a second average path length of said second wavelength that is greater than said first average path length; and said comparator further constructed to compare, at said second wavelength, said first and second portions of the delivered light to monitor a concentration of one or more of said solutes in said biological system.

38. The system of claim 17, 31, 34, 18, 19, 20 or 21 wherein said source-detector arrangement is constructed to deliver said light to one of the following: the finger, the arm, the head, the belly, and the liver.

39. The system of claim 17, 31, 34, 18, 19, 20 or 21 wherein said solute is one of the following: a low molecular weight carbohydrate, an alcohol, or an electrolyte.

40. The system of claim 17, 31, 34, 18, 19, 20 or 21 wherein said solute is one of the following: mannitol, fructose, sucrose, glucose, propanediol, methanol, ethanol, sodium ion, potassium ion, and chloride ion.

41. The system of claim 17, 31 or 34 wherein said source-detector arrangement is constructed to vary said average path lengths depending on an examined organ of said biological system.

42. The system of claim 41 wherein said organ is the liver.

43. A system for in vivo monitoring one or more solutes in a biological system comprising:

a source-detector arrangement formed by at least one light source constructed to deliver into a biological system light of a wavelength in a visible or infrared range, said wavelength exhibiting substantially no measurable absorption variation for one or more solutes present in said biological system, and at least one light detector constructed to detect light of said wavelength that has migrated in said biological system;

said source-detector arrangement constructed to provide at least first and second reference intensities ($I_{1,ref}$, $I_{2,ref}$) corresponding to first and second portions of said delivered light, said first portion having traveled through said biological system along photon migration paths characterized by a first average path length, and said second portion having traveled through said biological system along photon migration paths characterized by a second average path length that is greater than said first average path length;

said source-detector arrangement also constructed to provide over time at least first and second intensities ($I_1$, $I_2$); and a comparator constructed and arranged to determine relative changes, over time, in said first and second intensities ($I_1$, $I_2$) relative to first and second reference intensities ($I_{1,ref}$, $I_{2,ref}$) to monitor a measure of a concentration of one or more of said solutes in said biological system.

44. The system of claim 43 wherein said comparator further determines first and second optical densities ($OD_1$, $OD_2$) wherein $$OD_1 = \log\left(\frac{I_1}{I_{1,ref}}\right)$$

and $$OD_2 = \log\left(\frac{I_2}{I_{2,ref}}\right).$$

45. The system of claim 44 wherein said comparator employs a linear model relating said first and second optical densities to distances ($\rho_1$, $\rho_2$) representative of said first and second average path lengths to obtain a characterization of said biological system representative of the concentration of one or more of said solutes in said biological system.

46. The system of claim 45 wherein said comparator obtains said characterization by calculating a slope (m) determined by $$m = \frac{OD_2 - OD_1}{\rho_2 - \rho_1}.$$

47. The system of claim 45 wherein said comparator obtains said characterization by calculating an intercept (b) determined by $$b = \frac{OD_1 \cdot \rho_2 - OD_2 \cdot \rho_1}{\rho_2 - \rho_1}.$$

48. A system for in vivo monitoring one or more solutes in a biological system comprising:

a source-detector arrangement formed by at least one light source constructed to deliver into a biological system light of a wavelength in a visible or infrared range, said wavelength exhibiting substantially no measurable absorption variation for one or more solutes present in said biological system, and at least one light detector constructed to detect light of said wavelength that has migrated in said biological system, said source-detector arrangement constructed to provide at least first and second detected portions of said delivered light, said first portion having traveled through said biological system along photon migration paths characterized by a first average path length, and said second portion having traveled through said biological system along photon migration paths characterized by a second average path length that is greater than said first average path length, a control constructed and arranged to adjust a relationship between said detected first and second portions and said first and second average path lengths according to a known model thereby obtaining selected initial values of said first and second portions;

a comparator constructed and arranged to compare said detected first and second portions to said initial values of said first and second portions, respectively, according to said model; and said comparator also constructed and arranged to monitor a measure of a concentration of one or more of said solutes in said biological system based on said compared first and second portions.

49. The system of claim 48 wherein said comparator is further constructed and arranged to employ a predetermined concentration scale of said solute.

50. The system of claim 48 wherein said comparator is further constructed and arranged to monitor a variable proportional to the scattering coefficient of said biological system.